United States Patent
Inoue

(10) Patent No.: US 9,955,989 B2
(45) Date of Patent: May 1, 2018

(54) MANIPULATOR HAVING AT LEAST ONE JOINT ACTUATED BY DISPLACEMENT OF A DISPLACEABLE MEMBER

(71) Applicant: OLYMPUS CORPORATION, Tokyo (JP)

(72) Inventor: Shintaro Inoue, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 0 days. days.

(21) Appl. No.: 15/396,949

(22) Filed: Jan. 3, 2017

(65) Prior Publication Data

US 2017/0112519 A1 Apr. 27, 2017

Related U.S. Application Data

(63) Continuation of application No. PCT/JP2015/069593, filed on Jul. 8, 2015.

(30) Foreign Application Priority Data

Jul. 10, 2014 (JP) ................. 2014-142496

(51) Int. Cl.
*B25J 3/00* (2006.01)
*B25J 13/02* (2006.01)
(Continued)

(52) U.S. Cl.
CPC .......... *A61B 17/2909* (2013.01); *A61B 34/74* (2016.02); *B25J 3/00* (2013.01);
(Continued)

(58) Field of Classification Search
CPC ........ A61B 17/2909; A61B 34/74; B25J 3/00; B25J 13/02
(Continued)

(56) References Cited

U.S. PATENT DOCUMENTS 5,389,849 A * 2/1995 Asano ................. B25J 3/04
310/323.21
5,836,869 A * 11/1998 Kudo ................. A61B 1/00039
600/102

(Continued)

FOREIGN PATENT DOCUMENTS

EP 2982332 A1 2/2016
JP 2005-312919 A 11/2005
(Continued)

OTHER PUBLICATIONS

International Search Report dated Oct. 13, 2015 issued in PCT/JP2015/069593.

*Primary Examiner* — Paul T Chin
(74) *Attorney, Agent, or Firm* — Scully, Scott, Murphy & Presser, P.C.

(57) ABSTRACT

A manipulator including an elongated shaft, at least one joint disposed at a distal end of the shaft, a manipulating part via which a movement instruction for the joint is input, and a driving unit that drives the joint according to the movement instruction input via the manipulating part. The manipulating part includes a handle fixed to the shaft and gripped in one hand of an operator, a displaceable member that is disposed at a position along which at least one finger of the hand gripping the handle can be extended and that can be displaced by a movement of the finger extending therealong, and a sensor that detects displacement of the displaceable member and outputs it as the movement instruction.

10 Claims, 15 Drawing Sheets

(51) Int. Cl.
*A61B 17/29* (2006.01)
*A61B 34/00* (2016.01)
*A61B 17/00* (2006.01)

(52) U.S. Cl.
CPC ..... *B25J 13/02* (2013.01); *A61B 2017/00424* (2013.01); *A61B 2017/2908* (2013.01); *A61B 2017/2925* (2013.01); *A61B 2562/0261* (2013.01)

(58) Field of Classification Search
USPC .............. 294/209, 907; 901/2; 606/130
See application file for complete search history.

(56) References Cited

U.S. PATENT DOCUMENTS

| | | |
|---|---|---|
| 2002/0040217 A1 | 4/2002 | Jinno |
| 2004/0267406 A1 | 12/2004 | Jinno |
| 2005/0187575 A1 | 8/2005 | Hallbeck et al. |
| 2005/0222587 A1 | 10/2005 | Jinno et al. |
| 2006/0167589 A1 | 7/2006 | Jinno |
| 2006/0190034 A1 | 8/2006 | Nishizawa et al. |
| 2008/0091072 A1 | 4/2008 | Omori et al. |
| 2008/0177134 A1 | 7/2008 | Miyamoto et al. |
| 2008/0232932 A1 | 9/2008 | Jinno |
| 2008/0262654 A1* | 10/2008 | Omori ............... A61B 90/96 700/245 |
| 2009/0030428 A1* | 1/2009 | Omori ............... A61B 34/70 606/130 |
| 2009/0088773 A1* | 4/2009 | Zhao ............... G06K 9/3241 606/130 |
| 2014/0148820 A1* | 5/2014 | Ogawa ............... A61B 17/29 606/130 |
| 2014/0148950 A1* | 5/2014 | Ogawa ............... B25J 13/02 700/257 |
| 2014/0160015 A1* | 6/2014 | Ogawa ............... B25J 13/02 345/156 |
| 2015/0321355 A1* | 11/2015 | Kishi ............... B25J 9/1697 606/130 |
| 2015/0327940 A1* | 11/2015 | Inoue ............... A61B 34/30 606/130 |
| 2015/0342689 A1* | 12/2015 | Kamon ............... A61B 34/74 606/130 |
| 2016/0058514 A1 | 3/2016 | Ogawa et al. |
| 2016/0120612 A1* | 5/2016 | Yorimoto ........... A61B 18/1492 606/130 |

FOREIGN PATENT DOCUMENTS

| | | |
|---|---|---|
| JP | 2006-116194 A | 5/2006 |
| JP | 2006-218281 A | 8/2006 |
| JP | 2007-526805 A | 9/2007 |
| JP | 4014792 B2 | 11/2007 |
| JP | 2008-093270 A | 4/2008 |
| WO | WO 2005/079333 A2 | 9/2005 |
| WO | WO 2014/156250 A1 | 10/2014 |

* cited by examiner

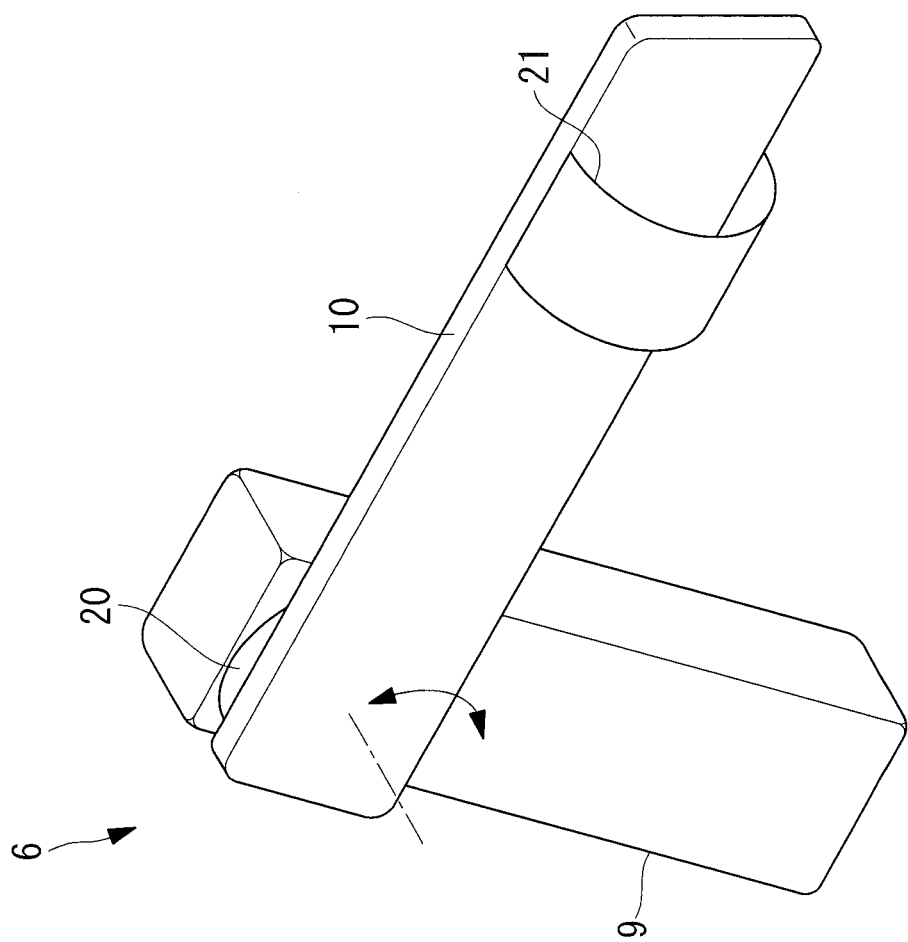

MANIPULATOR HAVING AT LEAST ONE JOINT ACTUATED BY DISPLACEMENT OF A DISPLACEABLE MEMBER

CROSS-REFERENCE TO RELATED APPLICATIONS

This is a continuation of International Application PCT/JP2015/069593 which is hereby incorporated by reference herein in its entirety.

This application is based on Japanese Patent Application No. 2014-142496, the contents of which are incorporated herein by reference.

TECHNICAL FIELD

The present invention relates to manipulators.

BACKGROUND ART

In a known manipulator used in laparoscopic surgery, a joint disposed at a distal end of a shaft that is passed through a trocar disposed in an opening provided in the skin is manipulated using a manipulating part disposed at a proximal end of the shaft (for example, see PTL 1).

In this manipulator, the manipulating part is provided with a handle that is gripped by an operator, the amount of bend and the direction of bend of the wrist of the hand that grips the handle are detected, and the joint is flexed in the corresponding direction and by the corresponding amount.

CITATION LIST

Patent Literature

{PTL 1} The Publication of Japanese Patent No. 4014792

SUMMARY OF INVENTION

Solution to Problem

An aspect of the present invention is a manipulator including: an elongated shaft; at least one joint disposed at a distal end of the shaft; a manipulating part via which a movement instruction for the joint is input; and a driving unit that drives the joint according to the movement instruction input via the manipulating part. The manipulating part includes a handle fixed to the shaft and gripped in one hand of an operator, a displaceable member that is disposed at a position along which at least one finger of the hand gripping the handle can be extended and that can be displaced by a movement of the finger extending therealong, and a sensor that detects displacement of the displaceable member and outputs it as the movement instruction.

BRIEF DESCRIPTION OF DRAWINGS

FIG. 9 is a fourth modification of FIG. 2, and is a perspective view showing a manipulating part to which an encoder for detecting pivoting of the displaceable member is attached.

DESCRIPTION OF EMBODIMENTS

A manipulator according to an embodiment of the present invention will be described below with reference to the drawings.

Figure 1:
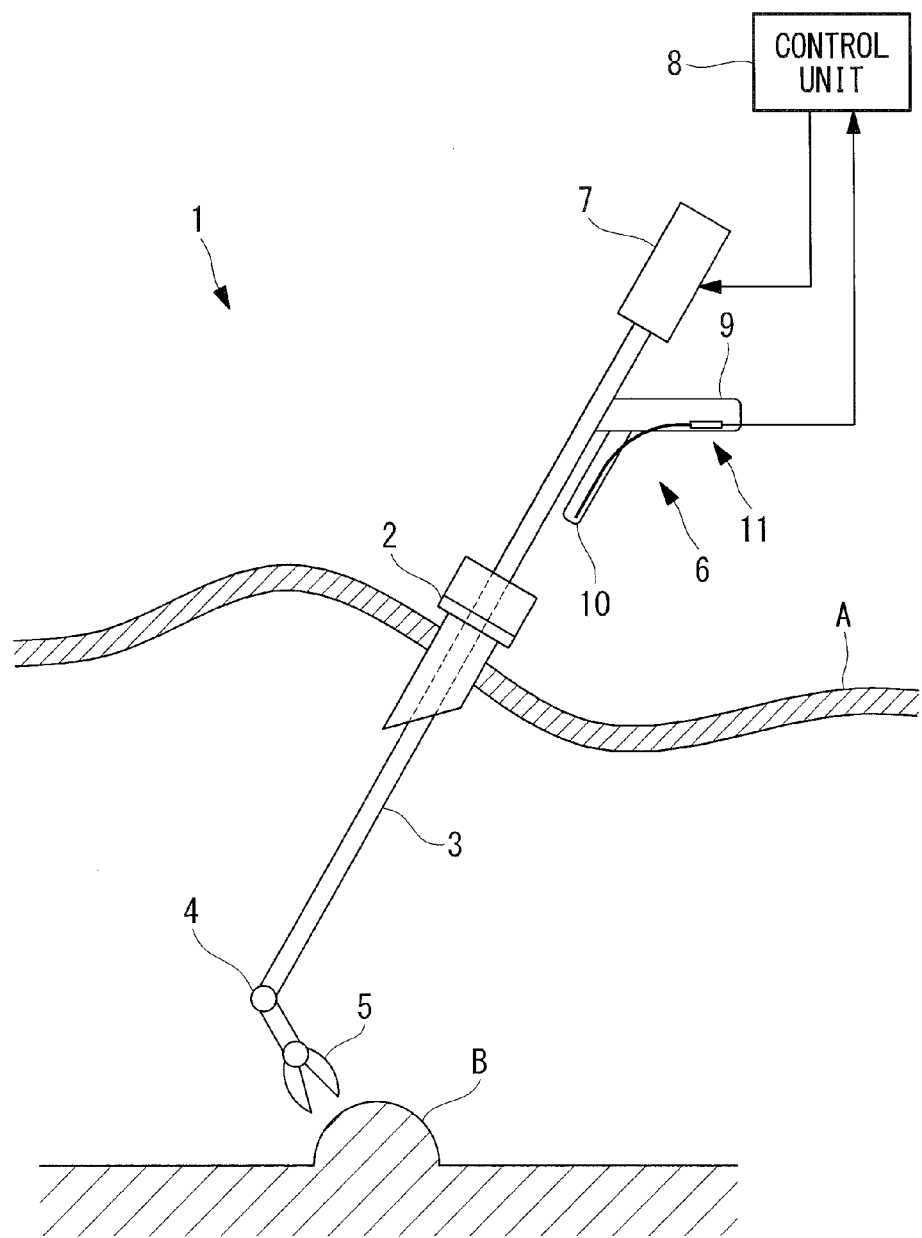
FIG. 1 is a diagram showing the overall configuration of a manipulator according to an embodiment of the present invention.

As shown in FIG. 1, a manipulator 1 according to this embodiment is used in, for example, laparoscopic surgery and includes an elongated shaft 3 to be inserted through a trocar 2 disposed so as to pass through skin A, a joint 4 disposed at a distal end of the shaft 3, a treatment instrument 5 disposed at a distal end of the joint, a manipulating part 6 for manipulating the joint 4, a driving unit 7 that drives the joint 4, and a control unit 8 that controls the driving unit 7.

The shaft 3 is formed in the form of, for example, a rigid cylinder, through which wires and cables (not shown) for driving the joint 4 and the treatment instrument 5 are disposed. In the example shown in FIG. 1, the joint 4 is a flexible joint that supports a distal end part, including the treatment instrument 5, in a manner allowing pivoting about an axis perpendicular to a longitudinal axis of the shaft 3. The treatment instrument 5, such as a grasping forceps or an energy forceps, is used to treat an affected area B within the body.

Figure 2:
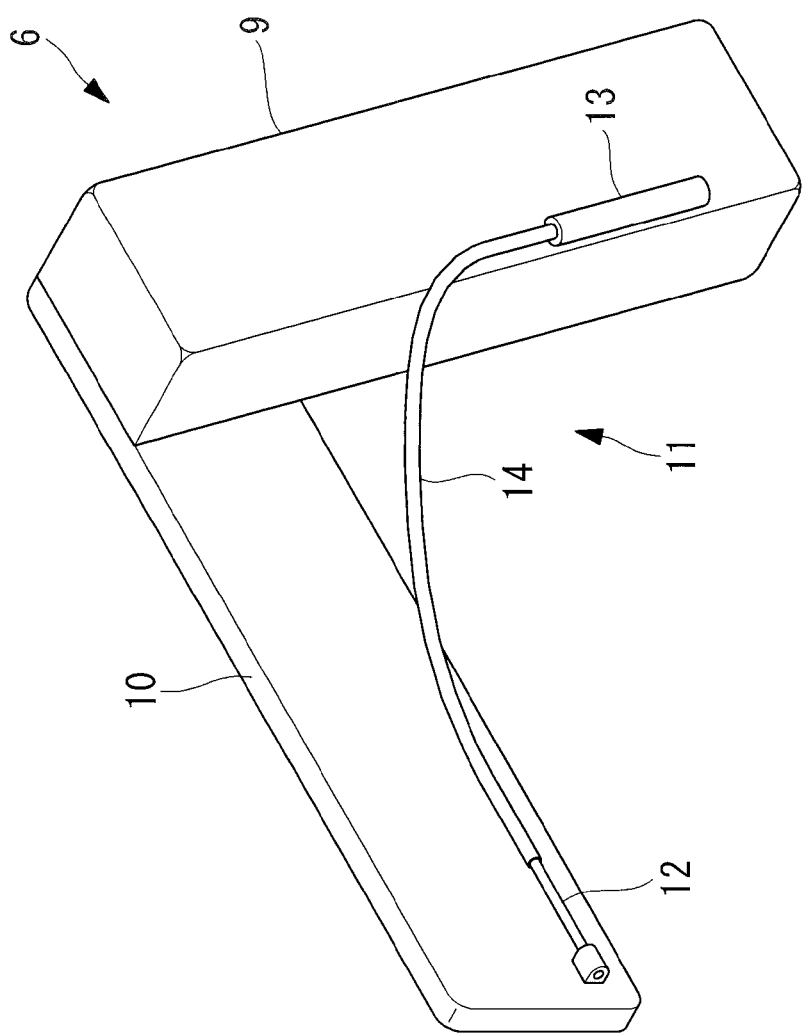
FIG. 2 is a perspective view showing a manipulating part of the manipulator in FIG. 1.

The manipulating part 6 includes, as shown in FIG. 1, a handle 9 fixed at an intermediate position, in the longitudinal direction, of the shaft 3 and, as shown in FIG. 2, a plate spring (displaceable member) 10 fixed in a cantilever manner to the handle 9, and a sensor 11 for detecting the amount of displacement of the distal end position of the plate spring 10.

Figure 3:
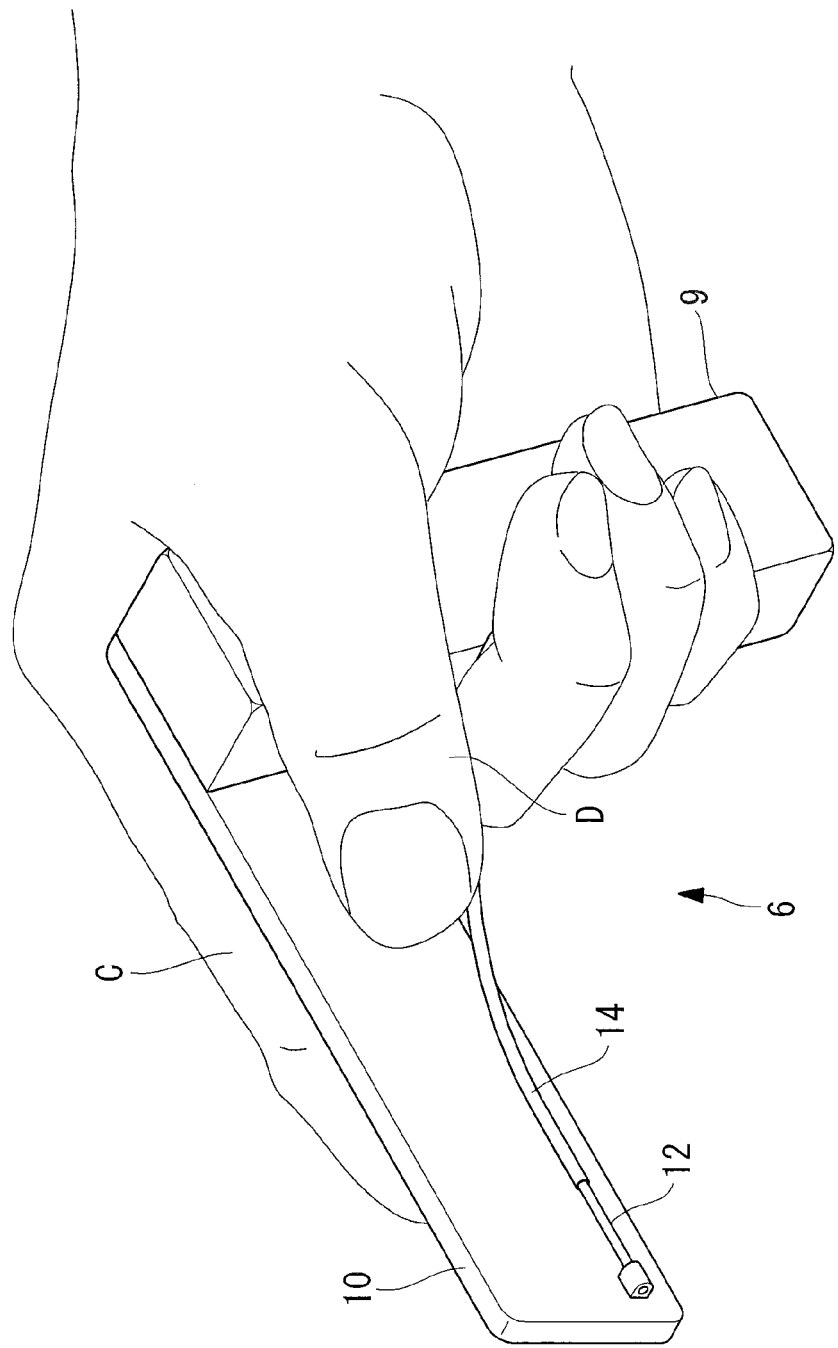
FIG. 3 is a perspective view showing a state in which the manipulating part in FIG. 2 is gripped in a right hand.

The handle 9 is formed in the shape of, for example, a quadrangular prism, and, as shown in FIG. 3, is gripped by the palm, middle finger, ring finger, and little finger of the right hand of an operator.

The plate spring 10 is formed of a strip-shaped flat plate and is disposed at a position along which the index finger is placed in the longitudinal direction when the operator extends his/her index finger straight, with the handle 9 being gripped in the right hand.

The sensor 11 includes, for example, a wire 12, which is formed of a magnetic material and one end of which is connected to a pivotable end of the plate spring 10, and a magnetic sensor 13, into which the other end of the wire 12 is inserted so as to be movable in the longitudinal direction and in which the voltage varies according to the insertion length thereof. The magnetic sensor 13 is fixed to, for example, the handle 9. Furthermore, reference sign 14 denotes a sheath that covers the wire 12 in such a manner as to allow the wire 12 to move.

The driving unit 7 is, for example, a motor that applies a pulling force to the wire passing through the shaft 3 to drive the joint 4.

The control unit 8 receives an output from the sensor 11 and outputs, to the driving unit 7, a driving instruction corresponding to the output.

The operation of the thus-configured manipulator 1 according to this embodiment will be described below.

When the affected area B within the body is to be treated by using the manipulator 1 according to this embodiment, as shown in FIG. 1, the shaft 3 is inserted, from the distal end of the manipulator 1, through the through-hole in the trocar 2 that is disposed so as to pass through the skin A, and the treatment instrument 5 and the joint 4 at the distal end are disposed inside the body.

In this state, the operator grips the handle 9 in the right hand and places an index finger C of the right hand along the plate spring 10, as shown in FIG. 3, while viewing, via a monitor, an image acquired by an endoscope (not shown) that is separately inserted into the body. Because the handle 9 is fixed to the shaft 3, by moving the handle 9, it is possible to move the shaft 3 in the longitudinal axis direction thereof or to move the shaft 3 such that the inclination angle thereof is changed, using the trocar 2 as the fulcrum.

Specifically, by moving the shaft 3, the position of the joint 4 disposed at the distal end of the shaft 3 can be adjusted.

Next, the operator flexes the plate spring 10 by bending the index finger C of the right hand, which grips the handle 9. Because the wire 12 is fixed to the distal end of the plate spring 10, when the plate spring 10 is flexed, and the distal end is displaced, the wire 12 moves within the sheath 14, and the insertion length of the other end of the wire 12 in the magnetic sensor 13 changes.

Figure 4A:
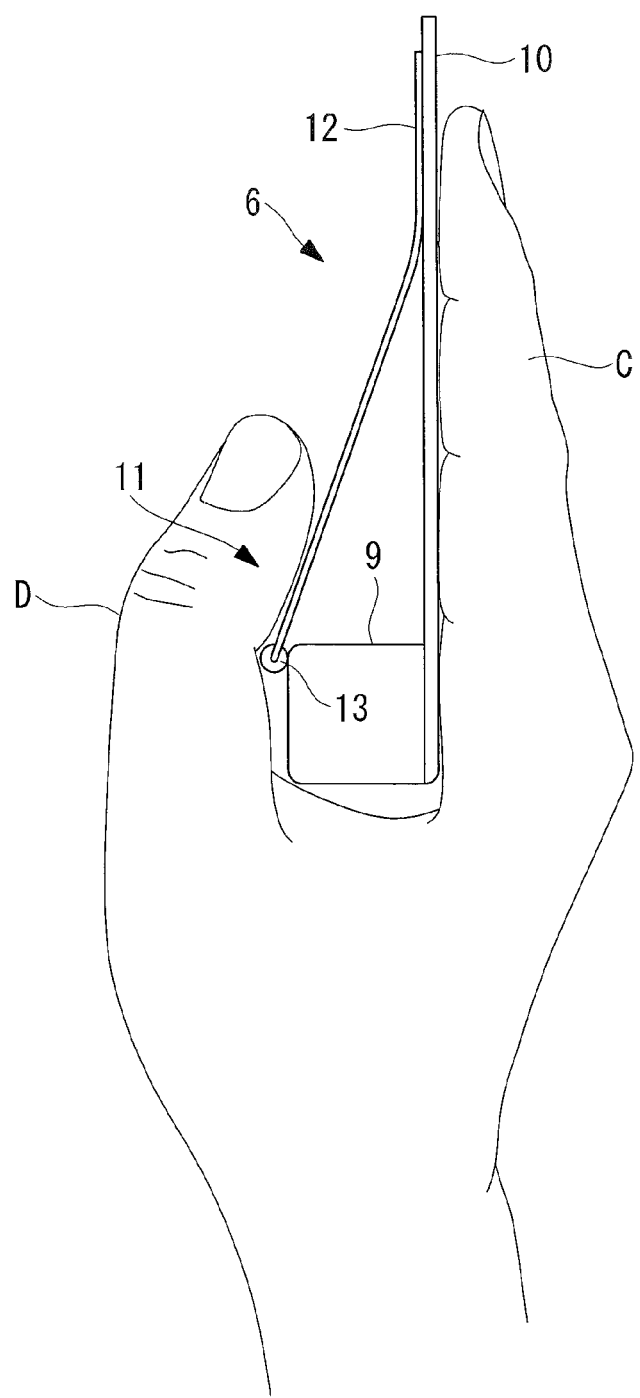
FIG. 4 is a plan view showing a state in which a force from a finger is not applied to a displaceable member.
FIG. 4B is a diagram showing a magnetic sensor in a state in which a force from a finger is not applied to the displaceable member.
Figure 4B:
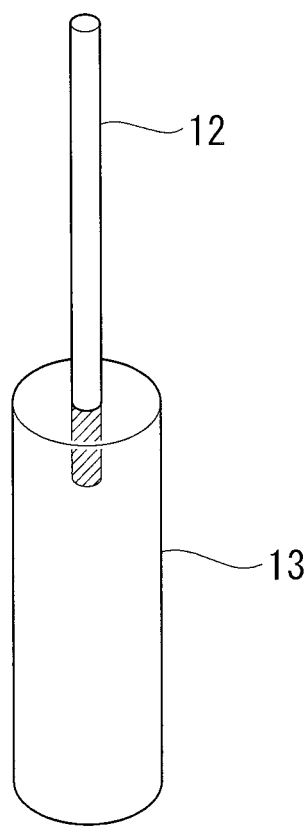
Figure 5A:
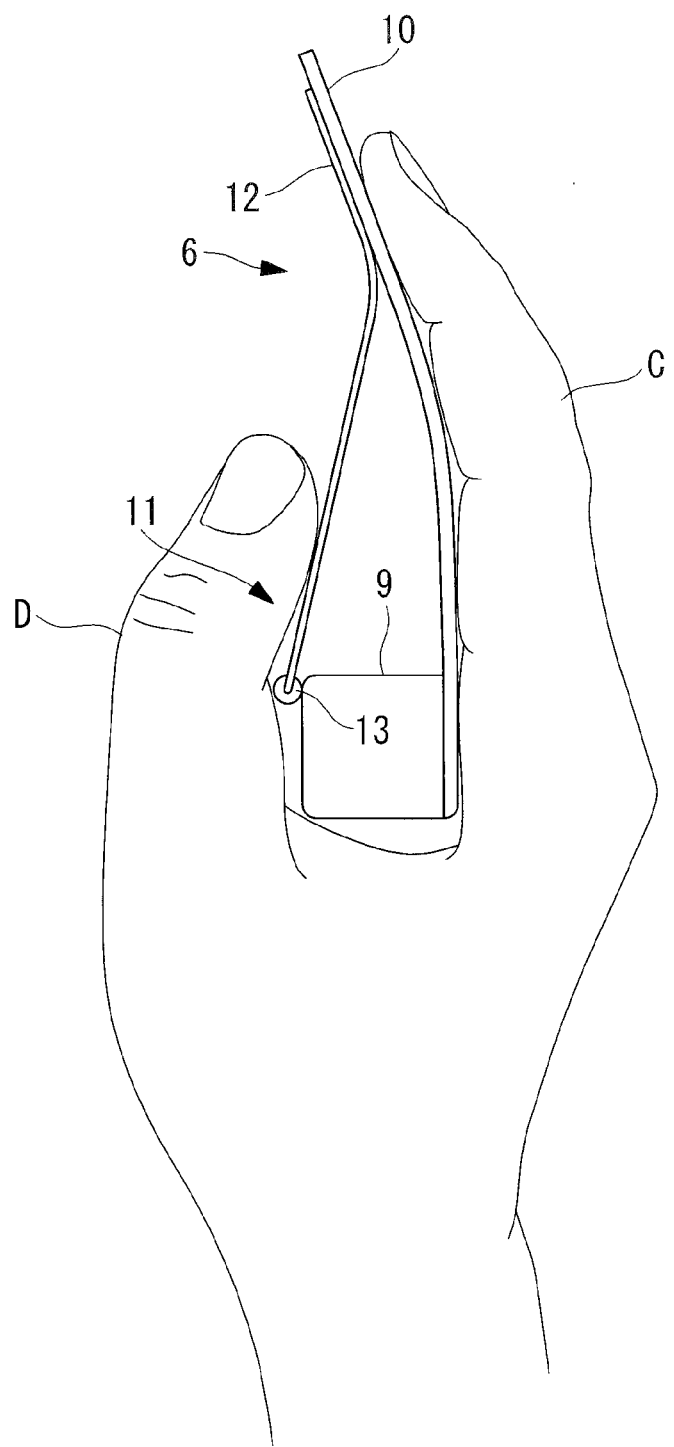
FIG. 5A is a plan view showing a state in which a force from a finger is applied to the displaceable member.
Figure 5B:
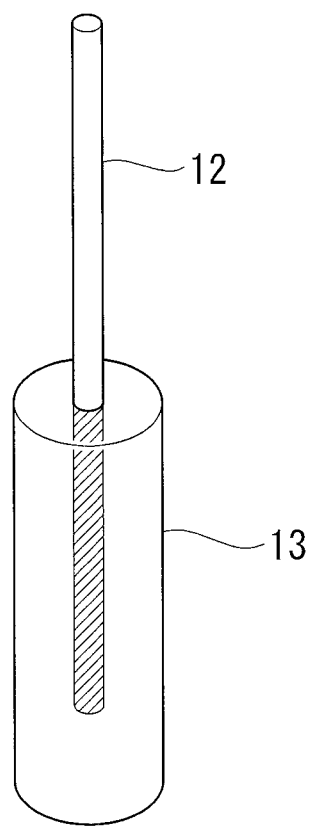
FIG. 5B is a diagram showing the magnetic sensor in a state in which a force from a finger is applied to the displaceable member.

Specifically, when the plate spring 10 is in a straight state, as shown in FIG. 4A, the insertion length of the wire 12 in the magnetic sensor 13 is small, as shown in FIG. 4B, whereas, when the plate spring 10 is in a flexed state, as shown in FIG. 5A, the insertion length of the wire 12 in the magnetic sensor 13 is large, as shown in FIG. 5B. Because the magnetic sensor 13 outputs a voltage corresponding to the insertion length of the wire 12, it is possible to detect the amount of displacement of the distal end of the plate spring 10 on the basis of the level of the output voltage.

When the amount of displacement of the distal end of the plate spring 10 detected by the magnetic sensor 13 is input to the control unit 8, the control unit 8 sends a driving instruction corresponding to the amount of displacement to the driving unit 7, and the driving unit 7 causes the joint 4 to flex by an angle corresponding to the driving instruction. Specifically, it is possible to change the direction of the treatment instrument 5 by flexing the joint 4 at the distal end of the shaft 3 by an amount corresponding to the amount by which the operator moves the index finger C of the right hand.

In this case, with the manipulator 1 according to this embodiment, the position of the joint 4 at the distal end of the shaft 3 can be adjusted according to the degree of bending of the wrist of the right hand or the amount of movement of the right arm, and the angle of movement of the joint 4 can be adjusted according to the degree of bending of the index finger C of the right hand. There is no need to move the index finger C when the wrist or the arm is moved, and conversely, there is no need to bend the wrist or the arm when the index finger C is moved. Specifically, it is possible to perform position adjustment of the joint 4 and flexing action of the joint 4 independently, i.e., without interfering with each other, which leads to an advantage in that it is possible to move the treatment instrument 5 intuitively and in a desired way.

Furthermore, according to this embodiment, because the displaceable member is formed of the plate spring 10, when the operator releases the force from the index finger C, the plate spring 10 returns to a straight state, as shown in FIG. 4A, due to the elastic restoring force. Hence, it is possible to return the joint 4 to a neutral position only by relaxing the hand.

Figure 6:
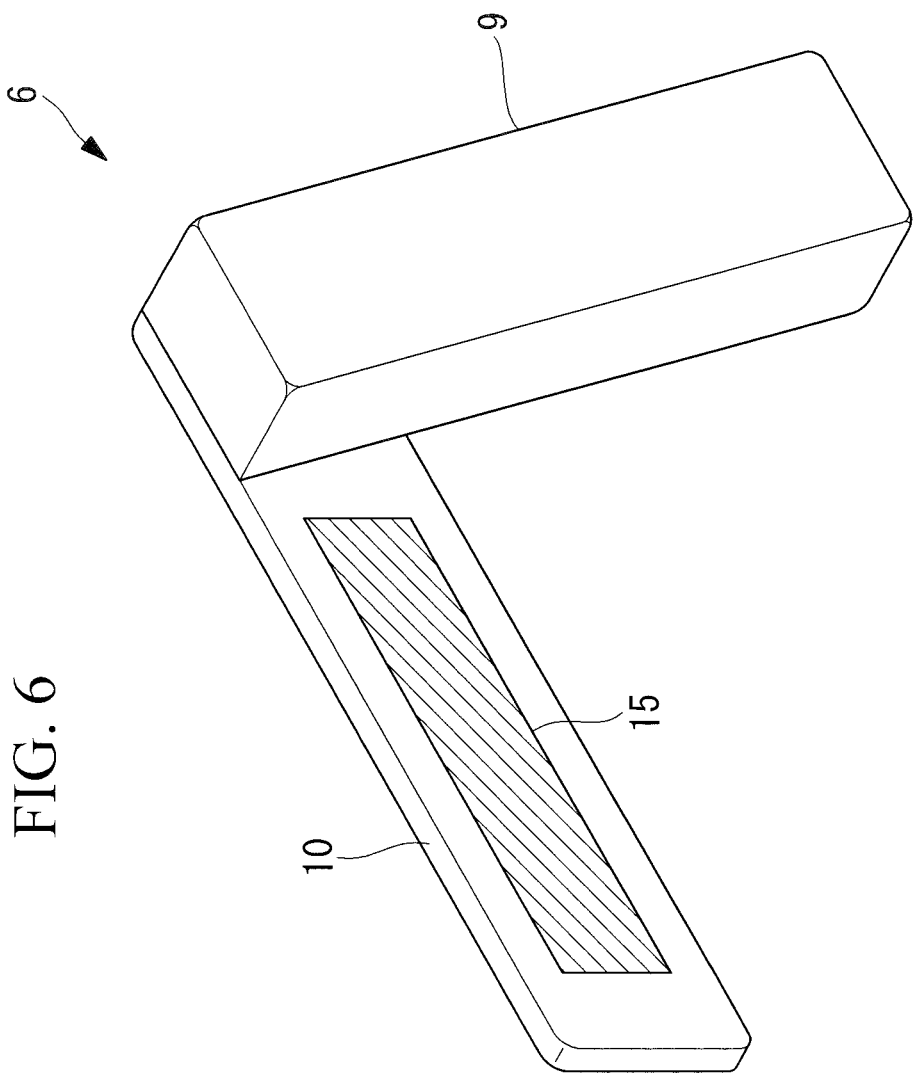
FIG. 6 is a first modification of FIG. 2, and is a perspective view showing a manipulating part to which a strain gauge, serving as a sensor for detecting the displacement of the displaceable member, is attached.

Although the amount of displacement of the plate spring 10 is detected with the wire 12 and the magnetic sensor 13 in this embodiment, instead, as shown in FIG. 6, it is possible to detect the amount of displacement of the plate spring 10 with a strain gauge 15 attached to the surface of the plate spring 10.

Figure 7:
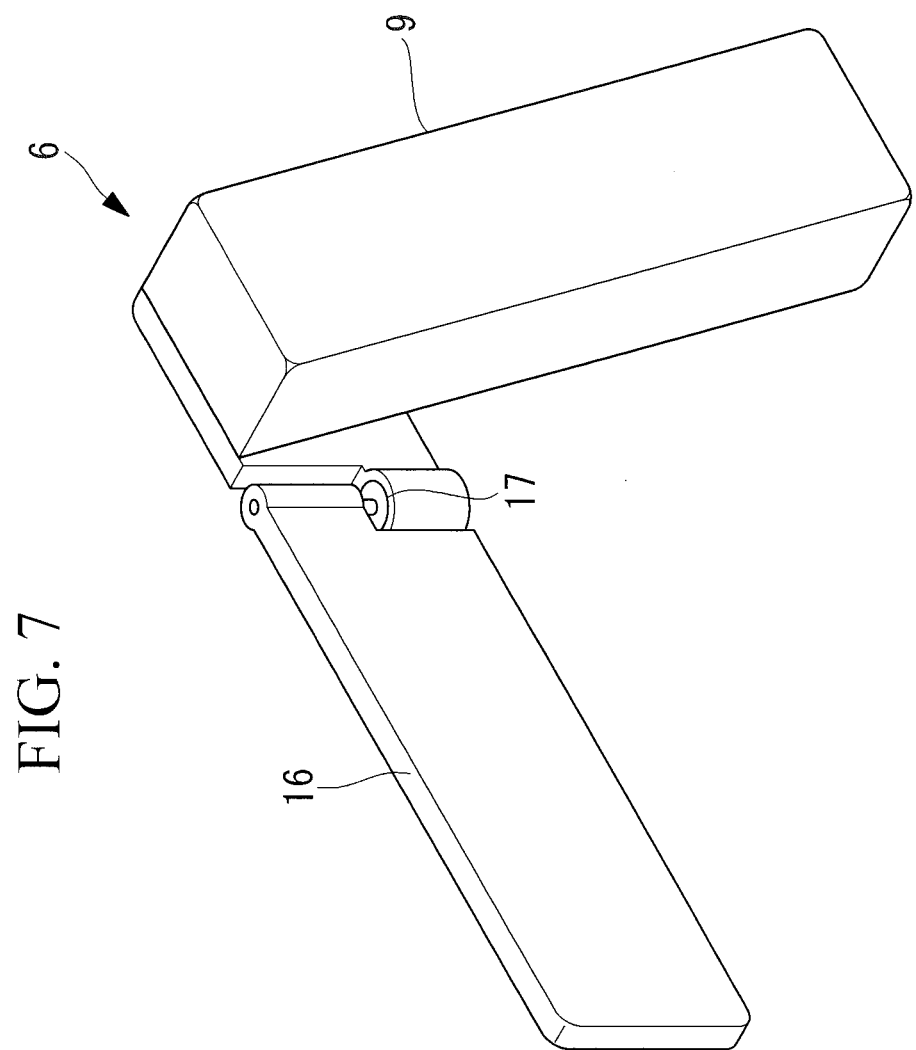
FIG. 7 is a second modification of FIG. 2, and is a perspective view showing a manipulating part to which an encoder, serving as a sensor for detecting the displacement of the displaceable member, is attached.

Furthermore, as shown in FIG. 7, instead of the plate spring 10, a flat plate member 16, serving as the displaceable member, may be pivotably supported by the handle 9, and the pivot angle of the flat plate member 16 relative to the handle 9 may be detected by an encoder 17.

Figure 8:
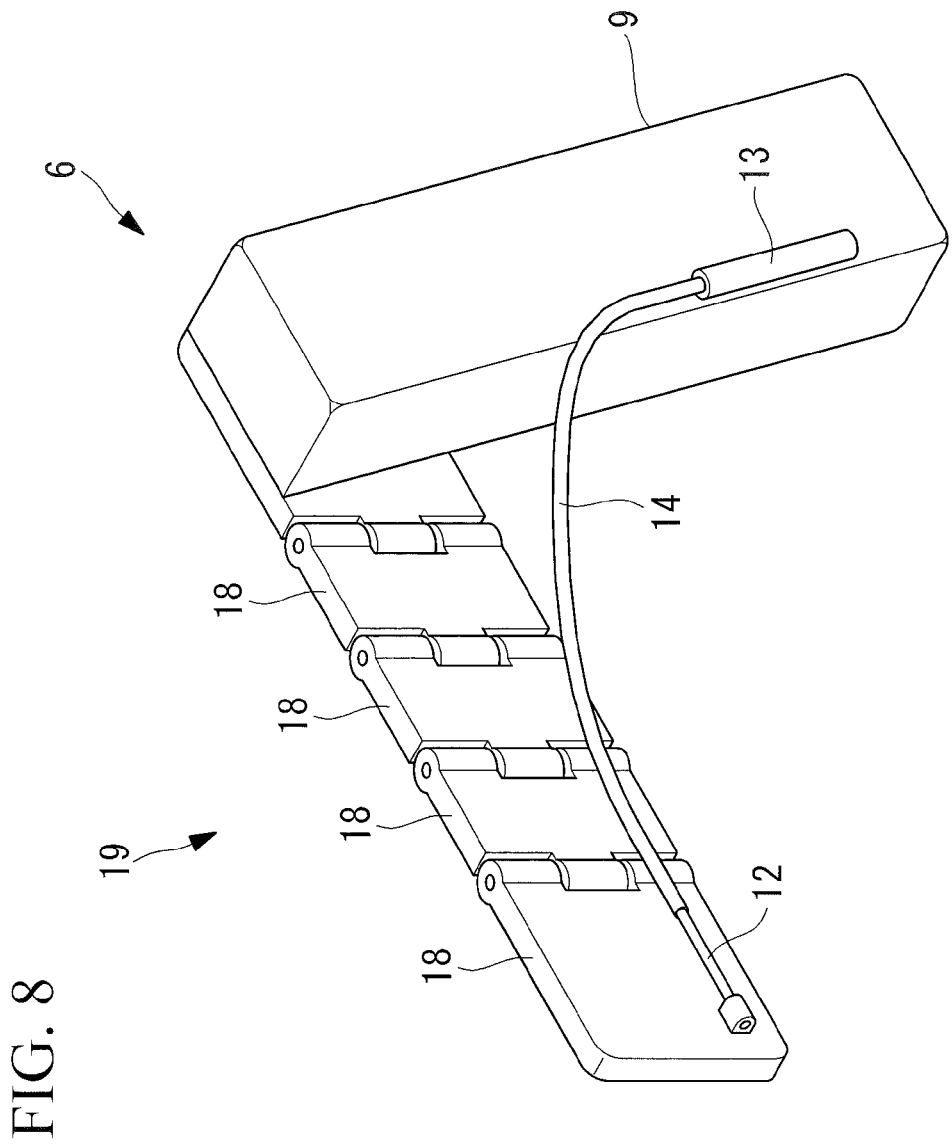
FIG. 8 is a third modification of FIG. 2, and is a perspective view of a manipulating part that includes a link mechanism serving as a displaceable member.

Furthermore, as shown in FIG. 8, instead of the plate spring 10, a link mechanism 19 formed of a plurality of pivotably joined links 18, serving as the displaceable member, may be employed. Furthermore, a displaceable member (not shown) in the form of a finger cot to be put on the index finger C may be employed.

Furthermore, as shown in FIG. 9, the plate spring 10 may be attached to the handle 9 so as to be pivotable in a direction perpendicular to the displacement direction thereof, and an encoder (second sensor) 20 for detecting the pivot angle may be provided.

With this configuration, it is possible to flex the plate spring 10 by bending the index finger C, actuating the joint 4 at the distal end of the shaft 3, and to pivot the plate spring 10 by moving the joint at the base of the index finger C, actuating another joint at the distal end of the shaft 3. In other words, the manipulator 1 that has two joints at the distal end of the shaft 3 can be manipulated with the index finger C. In the drawing, reference sign 21 denotes a belt through which the end of the index finger C is passed so that the index finger C is maintained in a state extending along the displaceable member.

Figure 10A:
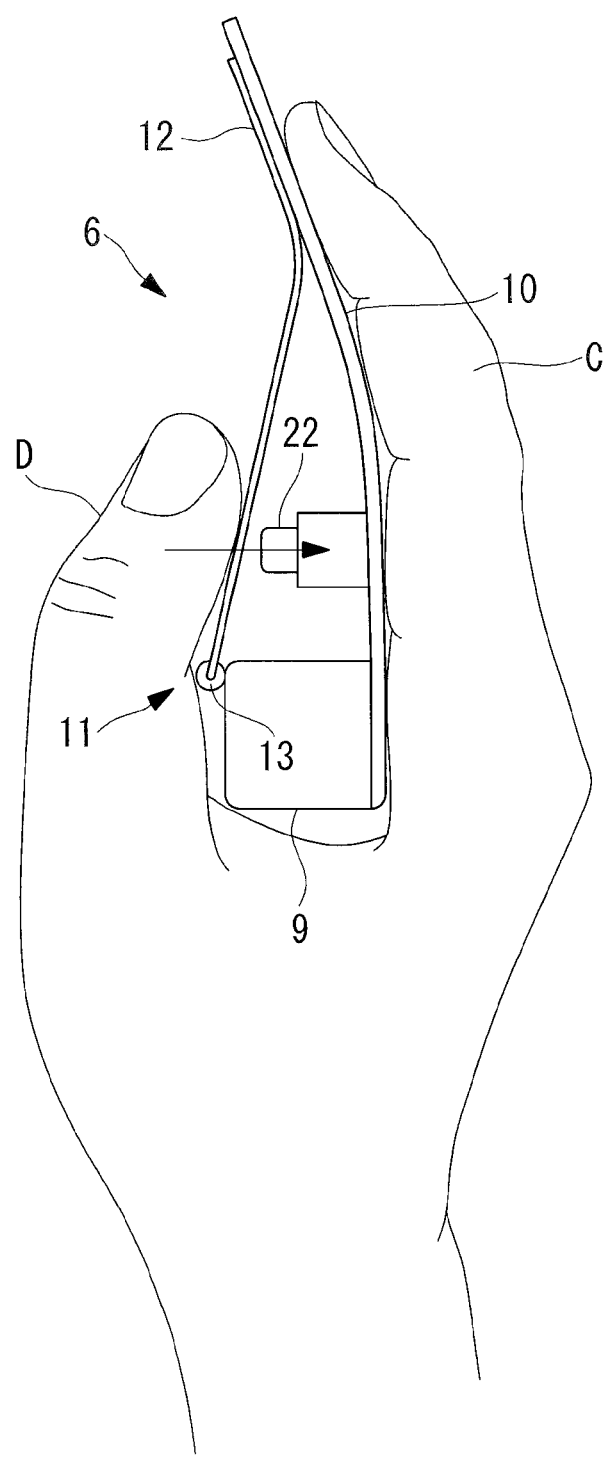
FIG. 10A is a plan view of a manipulating part in FIG. 2, provided with a switch for actuating a treatment instrument.
Figure 10B:
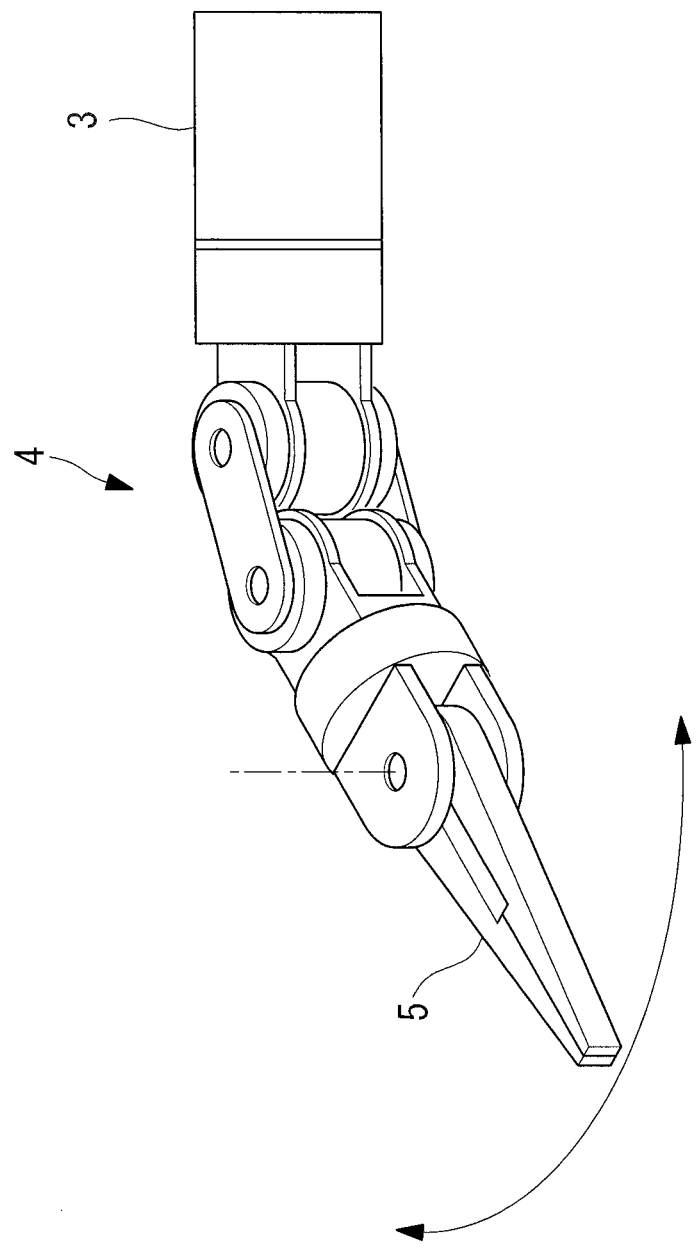
FIG. 10B is a perspective view showing a distal end part of the treatment instrument, in the manipulating part in FIG. 2, provided with a switch for actuating the treatment instrument.

Furthermore, as shown in FIG. 10A, a switch 22 for actuating the treatment instrument 5 may be provided at a position where it can be manipulated by a thumb D while the plate spring 10 is manipulated by the index finger C. For example, in the example shown in FIG. 10B, the switch 22 may be a switch for opening and closing the treatment instrument 5 that is formed of a grasping forceps. The position of the switch 22 is not limited to the position in FIG. 10A, as long as the switch 22 can be manipulated by the thumb D. The switch 22 may be provided at a position where it can be manipulated by a finger other than the index finger C or the thumb D.

Figure 11A:
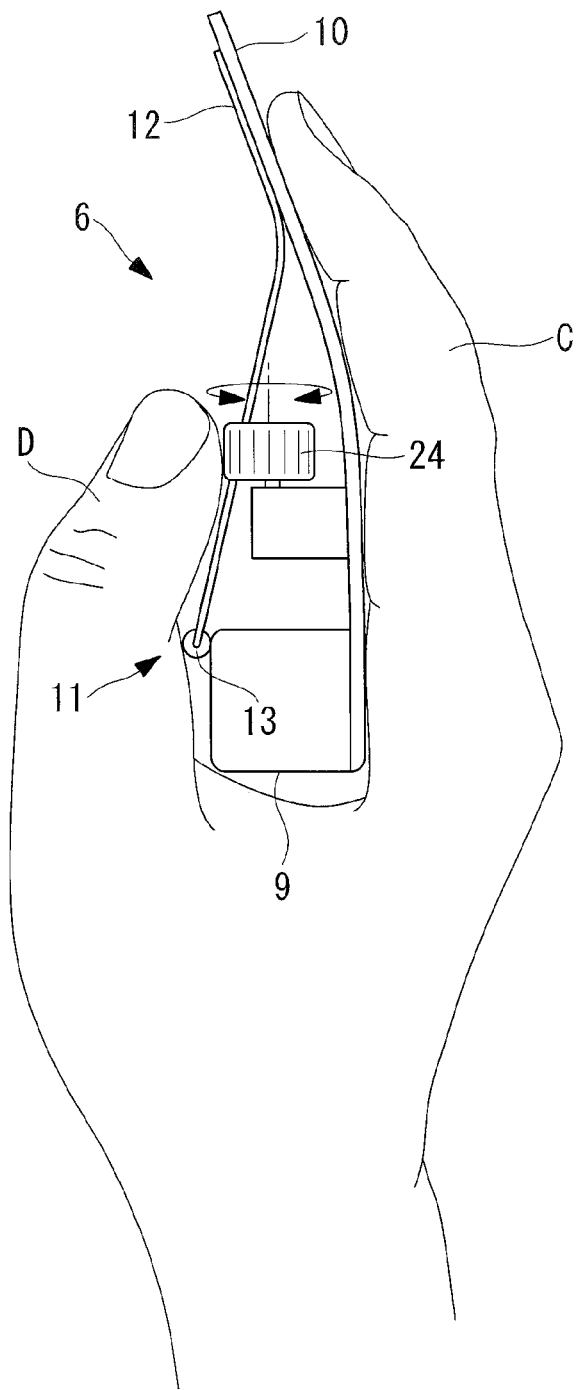
FIG. 11A is a plan view of a manipulating part in FIG. 2, provided with a dial for actuating another joint.
Figure 11B:
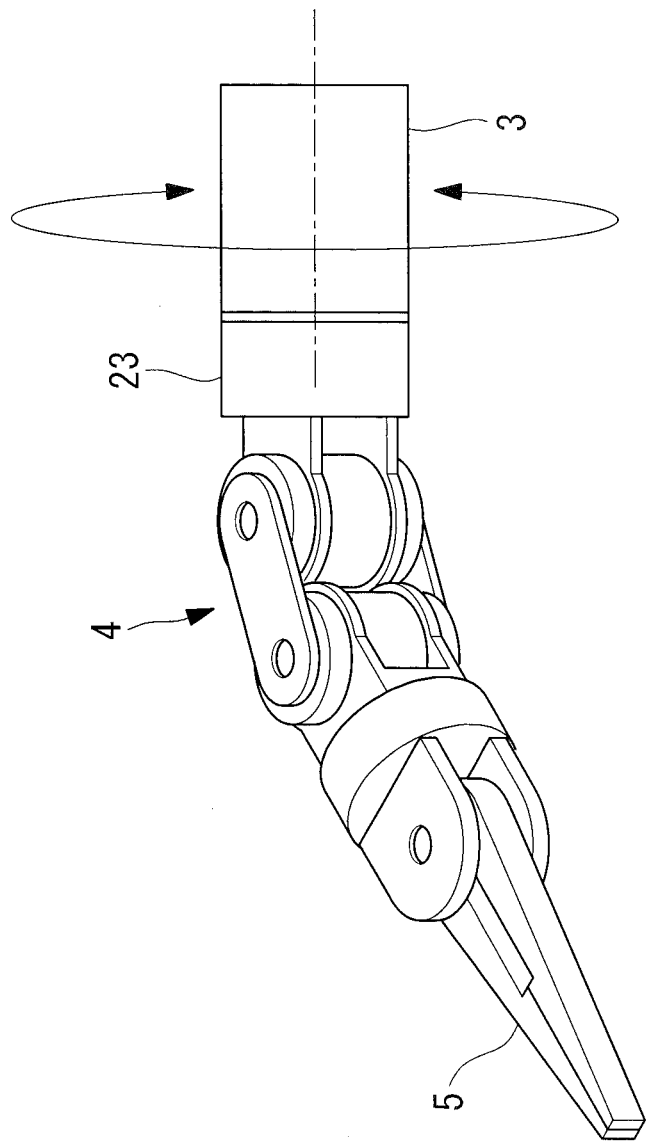
FIG. 11B is a perspective view showing a distal end part of a treatment instrument, in the manipulating part in FIG. 2, provided with a dial for actuating another joint.

Furthermore, as shown in FIG. 11A, a dial 24 for actuating a joint 23, as shown in FIG. 11B, other than the flexible joint 4 may be provided at a position where it can be manipulated by the thumb D while the plate spring 10 is manipulated by the index finger C. The position of the dial 24 is also not limited to the position in FIG. 11A, as long as the dial 24 can be manipulated by the thumb D. The dial 24 may be provided at a position where it can be manipulated by a finger other than the index finger C or the thumb D.

Furthermore, when the displaceable member is formed of the flat plate member 16, the link mechanism 19, or the like, as shown in FIG. 7 or 8, a clutch mechanism (not shown) may be disposed at a pivot axis of the flat plate member 16 or at the joints of the links 18 to maintain the displaceable member in a displaced state. By doing so, the joint 4 at the distal end of the shaft 3 can be maintained in a flexed state even after the force from the index finger C applied to the displaceable member is released. Hence, this is useful when another manipulation is performed while the joint 4 is maintained in the flexed state.

Furthermore, a reaction force to be transmitted toward the index finger C may be generated by employing a treatment instrument 5 including a force sensor (not shown), disposing motors at the joints of the links 18 of the displaceable member that is formed of the link mechanism 19, and feeding back the force detected by the force sensor to the driving unit 7. For example, when a retractor or a forceps is used as the treatment instrument 5, by generating a reaction force, the affected area B can be prevented from being subjected to an excessive load.

Furthermore, although an operator performs manipulation with his/her right hand in this embodiment, the manipulation may be performed with the left hand or with both hands. Furthermore, although an example case where manipulation is performed with the index finger C has been described, manipulation may be performed with another finger or with two or more fingers.

The above-described embodiment leads to the following inventions.

An aspect of the present invention is a manipulator including: an elongated shaft; at least one joint disposed at a distal end of the shaft; a manipulating part via which a movement instruction for the joint is input; and a driving unit that drives the joint according to the movement instruction input via the manipulating part. The manipulating part includes a handle fixed to the shaft and gripped in one hand of an operator, a displaceable member that is disposed at a position along which at least one finger of the hand gripping the handle can be extended and that can be displaced by a movement of the finger extending therealong, and a sensor that detects displacement of the displaceable member and outputs it as the movement instruction.

According to this aspect, when an operator grips the handle in one hand, at least one finger of that hand is disposed along the displaceable member. Hence, when the finger is moved to displace the displaceable member, the sensor detects the displacement, and the joint is driven by the driving unit according to the movement instruction corresponding to the displacement. Meanwhile, the position of the handle can be changed by bending the wrist of the hand that grips the handle, making it possible to move the shaft to which the handle is fixed and, hence, to change the position of the joint at the distal end of the shaft. Specifically, by individually allocating a finger and the wrist of a hand, which can be moved independently of each other, for changing the angle of movement of the joint and for changing the position of the joint, both movements can be performed without interfering with each other.

In the above aspect, the displaceable member may be a plate spring fixed to the handle in a cantilever manner.

With this configuration, when an operator bends the finger disposed along the displaceable member, the displaceable member, which is formed of a plate spring, receives a force from the finger and is flexed, displacing the respective parts. Hence, the amounts of displacement thereof can be easily retrieved. Furthermore, when the force from the finger is released, the displaceable member, which is formed of a plate spring, returns to its neutral position due to the elastic restoring force. Thus, the joint can be returned to the neutral position.

In the above aspect, the sensor may detect an amount of displacement of a distal end of the plate spring.

With this configuration, because the distal end of the plate spring supported in a cantilever manner is displaced by the greatest extent, it is possible to input the movement instruction at a high resolution.

In the above aspect, the sensor may be a strain gauge that detects, a strain of the plate spring.

With this configuration, simply by attaching a sensor formed of a strain gauge to the surface of the plate spring, it is possible to easily detect, with a compact configuration, the amount of displacement from the deformation of the plate spring.

In the above aspect, the displaceable member may be pivotably attached to the handle, and the sensor may be an encoder that detects a pivot angle of the displaceable member.

With this configuration, it is possible to precisely detect, with the encoder, the displacement of the displaceable member as a pivot angle, regardless of the spring rigidity of the displaceable member.

In the above aspect, the displaceable member may be attached to the handle so as to be pivotable in a direction intersecting a displacement direction of the displaceable member, and a second sensor that detects a pivot angle of the displaceable member may be provided.

With this configuration, by detecting the displacement of the displaceable member with the sensor and detecting the pivot angle of the displaceable member with the second sensor, it is possible to input movement instructions in two directions with a single displaceable member. Hence, two joints disposed at the distal end of the shaft can be independently driven.

In the above aspect, the manipulator may include an input part provided at a position where the input part can be manipulated by a finger that is different from the finger for displacing the displaceable member.

With this configuration, by manipulating the input part with a finger that is different from the finger for displacing the displaceable member, another input, such as an actuating instruction for an end effector disposed on a distal end side of the joint, may be performed.

REFERENCE SIGNS LIST

C index finger (finger)
1 manipulator 3 shaft
4 joint
6 manipulating part
7 driving unit
9 handle
10 plate spring (displaceable member)
11 sensor
15 strain gauge (sensor)
16 flat plate member (displaceable member)
17 encoder
19 link mechanism (displaceable member)
20 encoder (second sensor)
22 switch (input part)
24 dial (input part)

The invention claimed is:

1. A manipulator comprising:
an elongated shaft having a proximal end and a distal end, the shaft extending from the proximal end toward the distal end in a longitudinal direction thereof;
a treatment instrument that includes at least one joint disposed at the distal end of the shaft, the treatment instrument being configured to treat an object;
a manipulating part via which a movement instruction for the at least one joint is input; and
a driving unit that drives the at least one joint according to the movement instruction input via the manipulating part,
wherein the manipulating part includes:
a handle fixed to the proximal end of the shaft and gripped in one hand of an operator;
a displaceable member, so that at least one finger of the hand gripping the handle can be extended therealong, the displaceable member being fixed to the handle and extends along the shaft in the longitudinal direction of the shaft without contacting the shaft, the displaceable member being attached to the handle so as to be pivotable in a direction intersecting a longitudinal direction of the handle; and
a sensor that detects a displacement of the displaceable member and outputs the displacement as the movement instruction,
wherein the treatment instrument is manipulated by the at least one joint being actuated by the displacement of the displaceable member.

2. The manipulator according to claim 1, wherein the displaceable member is a plate spring fixed to the handle in a cantilever manner.

3. The manipulator according to claim 2, wherein the sensor detects an amount of displacement of a distal end of the plate spring.

4. The manipulator according to claim 2, wherein the sensor is a strain gauge that detects a strain of the plate spring.

5. The manipulator according to claim 2, wherein
the displaceable member is attached to the handle so as to be pivotable in a direction intersecting a displacement direction of the displaceable member, and
a second sensor that detects a pivot angle of the displaceable member is provided.

6. The manipulator according to claim 1, wherein
the displaceable member is pivotably attached to the handle, and
the sensor is an encoder that detects a pivot angle of the displaceable member.

7. The manipulator according to claim 1, further comprising an input part provided at a position where the input part can be manipulated by a finger that is different from the finger for displacing the displaceable member.

8. The manipulator according to claim 1,
wherein the displaceable member is formed of a plurality of links pivotably joined with each other in a longitudinal direction of the displaceable member, and
the displaceable member is displaced by bending the finger.

9. The manipulator according to claim 1, further comprising a dial connected with the displaceable member,
wherein the dial can be rotated by a finger of the hand which is different from the finger extending along the displaceable member to manipulate a joint which is disposed at the shaft and which is different from the at least one joint actuated by the displacement of the displaceable member.

10. The manipulator according to claim 1, further comprising a switch connected with the displaceable member,
wherein the switch can be manipulated by a finger of the hand which is different from the finger extending along the displaceable member to actuate the treatment instrument.

* * * * *